United States Patent [19]

Wang et al.

[11] Patent Number: 5,524,084

[45] Date of Patent: Jun. 4, 1996

[54] METHOD AND APPARATUS FOR IMPROVED FLOW AND PRESSURE MEASUREMENT AND CONTROL

[75] Inventors: Tak K. Wang, Havertown; Edwin E. Wikfors, Landenberg, both of Pa.

[73] Assignee: Hewlett-Packard Company, Palo Alto, Calif.

[21] Appl. No.: 366,532

[22] Filed: Dec. 30, 1994

[51] Int. Cl.⁶ .................................... G01F 1/12
[52] U.S. Cl. .................. 364/510; 364/509; 364/507; 73/23.22; 73/23.25; 73/204.19; 73/23.27
[58] Field of Search ................ 73/204, 203, 202; 62/181; 364/509, 510, 507; 55/20

[56] References Cited

U.S. PATENT DOCUMENTS

| | | | |
|---|---|---|---|
| 4,586,142 | 4/1986 | Cota et al. | 364/507 |
| 4,994,096 | 2/1991 | Klein et al. | 55/20 |
| 5,108,466 | 4/1992 | Klein et al. | |
| 5,476,000 | 12/1995 | Henderson et al. | 73/23.27 |

OTHER PUBLICATIONS

Lucas Control System Products, NOVASENSOR Sales Brochure, includes: Short Form Catelog,NPI Series All Media Solid State Sensor Pressure Transducer—Medium Pressure and High Pressure Brochures, NPH Series Solid State Pressure Sensor—Medium Pressure, and Low Pressure Brochures, NAS Series Solid State Accelerometer Signal Conditioned.
Output Brochure, NAC Series Silicon Accelerometers–Ceramic Packages Brochure.

*Primary Examiner*—Emanuel T. Voeltz
*Assistant Examiner*—Demetra R. Smith
*Attorney, Agent, or Firm*—Richard F. Schuette

[57] ABSTRACT

In the preferred embodiment, the invention is embodied in the pneumatic manifold of a gas chromatograph to provide current operating temperature and pressure compensation of inlet fluid flow. The pneumatic manifold comprises a plurality of thermally coupled mass flow, pressure and temperature sensors which generate signals related to mass flow of the fluid, fluid pressure and sensor temperature prior to the introduction of the fluid into the column. A plurality of firmware models which characterize the effects of current operating temperature and pressure variations on the mass flow and pressure sensors are stored in computer memory. Compensation is provided by determining the desired flow into the inlet, determining the control signal required to achieve this values at current operating conditions, determine the current operating conditions, implementation of firmware models to determine the effects on flow due to changes in current operating conditions and finally, generation of an adjustment to the control signal that nullifies the effects caused by changes in current operating conditions. These steps are repeated continuously to provide closed loop control of the desired detector conditions.

18 Claims, 8 Drawing Sheets

METHOD AND APPARATUS FOR IMPROVED FLOW AND PRESSURE MEASUREMENT AND CONTROL

FIELD OF THE INVENTION

The present invention relates to methods and apparatus for providing distribution, monitoring and regulation of fluids, and more particularly, to a temperature compensated mass flow and pressure sensor for use in a pneumatic manifold to provide accurate sensing and control of fluid pressure and flow.

BACKGROUND OF THE INVENTION

In the field of flow and pressure measurement it is well known to employ a hot wire anemometer to determine flow rates. A fluid is typically passed over a single heated wire, reducing the temperature of the wire. The change in resistance of the heated wire is determined and correlated with the flow rate of the gas. A more advanced technique employs two temperature sensing elements located a fixed and equal distance from a heat source. The fluid is passed through the system, reducing the temperature of the upstream sensor and increasing the temperature of the downstream sensor. The temperature difference is then recorded as an output signal.

A major drawback of hot wire anemometers is the non-linear, temperature and fluid-dependent manner in which they respond to fluid flow. A technique and method for linearizing output signals of such anemometers is disclosed in commonly assigned U.S. patent application Ser. No. 07/611,425 filed on Nov. 11, 1990, now abandoned entitled "Methods and Systems for Fluid Identification and Flow Rate Determination," the disclosure of which is herein incorporated by reference. Unfortunately, this technique does not adequately compensate for drift in the output signal associated with variations in operating temperatures and pressures (while this is typically referred to as ambient temperature and pressure, actual operating temperatures and pressures may vary with instrument construction).

In analytical instrumentation, there is a need for very accurate fluid flow which is compensated for changes in ambient, or current operating, temperature and pressure. In a gas chromatograph, the flow rate of the carrier gas is typically controlled by adjusting the pressure of the carrier gas updstream of a flow sensor. FIG. 1 illustrates a control valve 5 for controlling the flow of fluid 10 from a source 15 (illustrated as a cylinder of pressurized fluid, alternatively, fluid flow could be caused by a negative pressure on the downstream side of the control valve 5). The fluid 10 flows through a mass flow sensor 20 which generates an output voltage 25 corresponding to the mass flow of the fluid 10. The output voltage 25 provides feedback to control the opening and closing of the valve 5. As well known in the control feedback art, the ability of the mass flow sensor 20 to accurately sense and provide the output voltage 25 is very important to controlling flow and pressure.

The repeatability of the chromatographic output of the forward pressure regulated chromatographic apparatus 10 shown in FIG. 2 depends upon the output of the flow sensor 16. The sensor 16 may or may not be resident on the analytical instrument. The computer or microprocessor 24 then generates a feedback control signal 26 for controlling the opening and closing of valve 14 for regulation of the carrier fluid flow. The injection port 12 provides a portion of the carrier fluid/sample combination to a column 18, with the remainder passing through a non-analyzed output 20. Unfortunately, the feedback signal output by the flow sensor drifts with temperature variations and makes it difficult to accurately control the valve 14 and the corresponding flow rate. There exists a need for more stable inlet fluid flows and reduced manifold temperature variations to provide better chromatographic area repeatability as measured by the detector 30 at the end of the column 18.

One method for eliminating temperature sensitivity is to enclose the flow sensing devices in a temperature controlled zone, e.g., a "heated zone" constructed with thermally insulating material. Temperature sensors and heaters inside the heated zone provide feedback to maintain the flow restrictor and pressure sensor temperatures constant and thereby remove temperature as an error-producing variable.

Unfortunately, the incorporation of a heated zone increases manufacturing costs related to instrument calibration and components. Additionally, instrument reliability is reduced as the components required to regulate a heated zone are more likely to fail with continual operation at manifold temperatures higher than ambient. Furthermore, a heated zone requires a long start-up time components required to regulate a heated zone are more likely to fail with continual operation at manifold temperatures higher than ambient. Furthermore, a heated zone requires a long start-up time to stabilize prior to instrument operation.

A need exists for a flow sensor which automatically compensates for ambient temperature and pressure changes without the use of a heated zone.

SUMMARY OF THE INVENTION

The present invention provides a method and apparatus for accurate measurement of fluid flow. The output voltage of a flow sensor is modified by a drift voltage to compensate for the effect of variations in operating temperatures and pressure on the flow sensor output voltage. The drift voltage is determined by first generating a fluid flow equation which characterizes the expected flow sensor output voltage (Vo) in terms of fluid flow through the flow sensor. The first derivative of the fluid flow equation (dVo/dT) may then be used to characterize the effects of drifts in temperature and pressure. During operation of the flow sensor, measured flow rates and measured operating temperature and pressure values are substituted into the drift equation to determine the drift voltage. The drift voltage is then combined with the flow sensor output voltage to generate a modified flow sensor output voltage which is compensated for changes in operating temperature and pressure. The substitutions into the derivative of the flow equation and subsequent calculations required to obtain the drift voltage are repeated frequently to continually update the sensor $$Vo = \alpha * [1 - exp(\beta f)] + Voffset$$

where the constant $\alpha$ is proportional to the electronic gain and the temperature of a heating bridge within the flow sensor, and the constant $\beta$ is related to the thermal diffusity of the fluid being sensed.

A look-up table generated prior to operation of the flow sensor may be employed as an alternative embodiment to inputting the current temperature and pressure into the derivative of the flow equation each time the drift current is calculated. During operation, current operating temperature and pressure are measured and employed for accessing the corresponding drift voltage from the look-up table.

Fluid flow may be controlled by employing the modified output voltage as a feedback control signal for opening and closing a proportional valve. For example, forward pressure and back pressure regulation of inlet flows of a gas chromatograph may be accomplished through the use of a mass flow sensor having ambient temperature and pressure compensation to provide feedback to a proportional valve or valves, as well as a pressure sensor having ambient temperature and pressure compensation. The pressure sensor drift voltage is determined in a manner similar to the flow sensor drift voltage.

Recent advances in integrated circuit memory design, in particular, Electronically Erasable Programmable Memory (EEPROM) provide for storage of look-up table values in close proximity to the flow sensor. Mounting an EEPROM in combination with a flow sensor as a module makes it possible to calibrate the module in the factory or in the field, and ensure that the correct drift voltages are associated with the right flow sensor. If a flow sensor is changed in the field, it would be possible to calibrate and generate new drift voltages for storage into the EEPROM.

Other aspects and advantages of the present invention will become apparent from the following detailed description, taken in conjunction with the accompanying drawings, illustrating by way of example the principles of the invention.

DETAILED DESCRIPTION OF THE PREFERRED EMBODIMENTS

The present invention provides a method and apparatus for ambient temperature and pressure compensation of both flow and pressure sensors. Compensation is obtained by modifying flow and pressure sensor output voltages in accordance with a flow sensor drift voltage and a pressure sensor drift voltage. The drift voltages are obtained by generating models in firmware which characterize flow and pressure sensor response. The models are calibrated at known flows and pressures and may be accessed during sensor operation to provide the drift voltages. Alternatively, the models can be accessed prior to sensor operation for generating a look-up table of drift voltages over expected operating ranges. During operation, the look-up table is accessed in accordance with the measured temperature and pressure to obtain the corresponding drift voltage.

Figure 1:
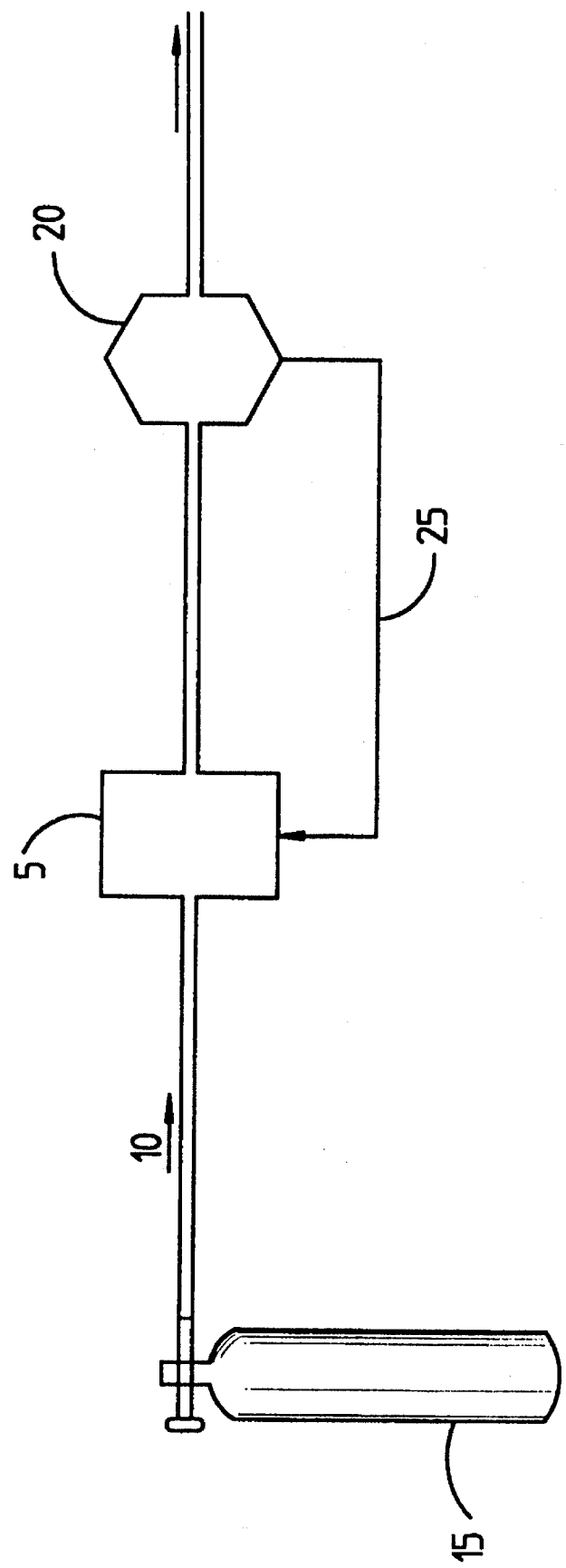
FIG. 1 is a simplified schematic representation of a non-temperature compensated flow regulating device well known in the prior art.
Figure 2:
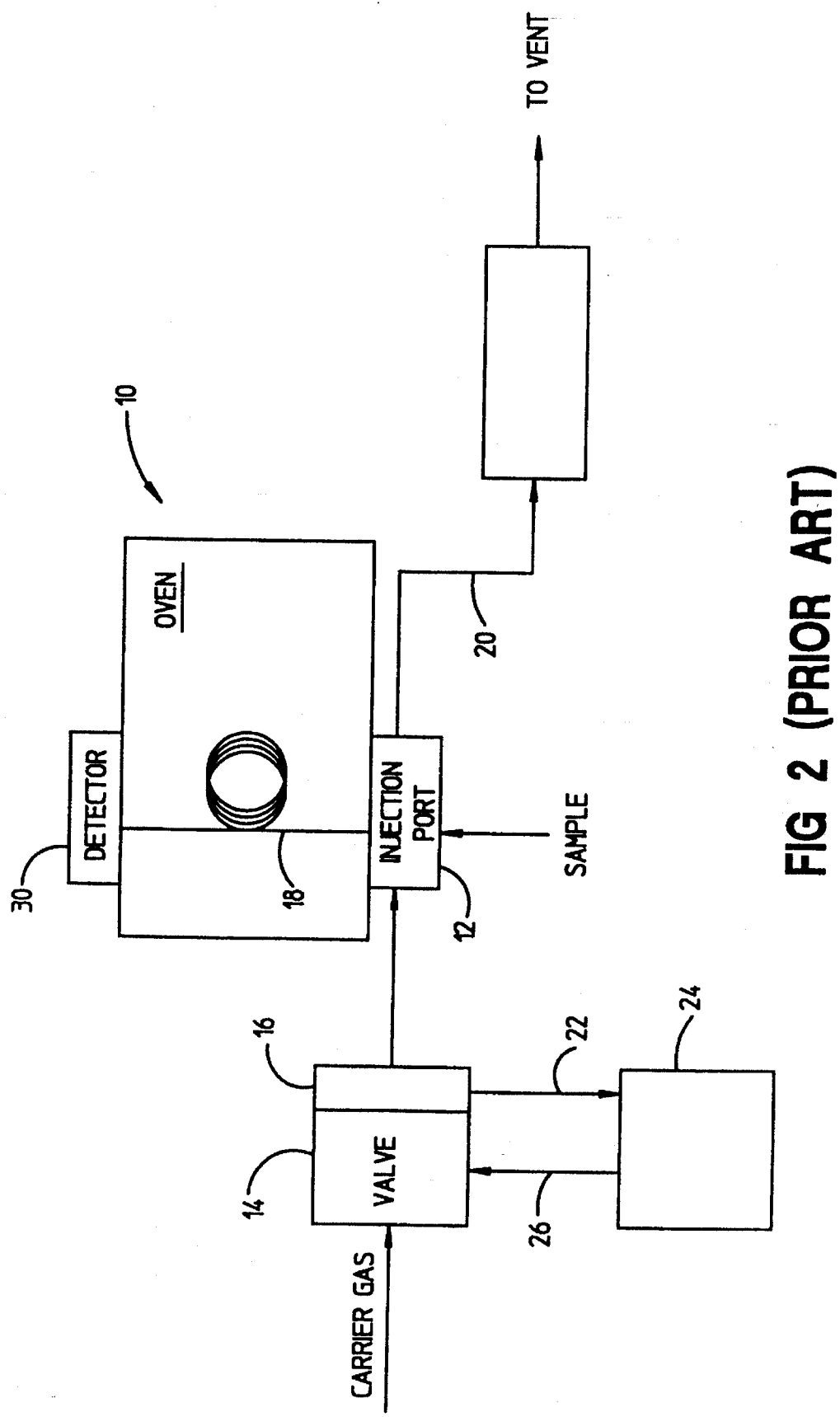
FIG. 2 is a schematic representation of a gas chromatograph employing a pressure sensor for regulating the carrier gas flowing into the inlet as known in the prior art.
Figure 3:
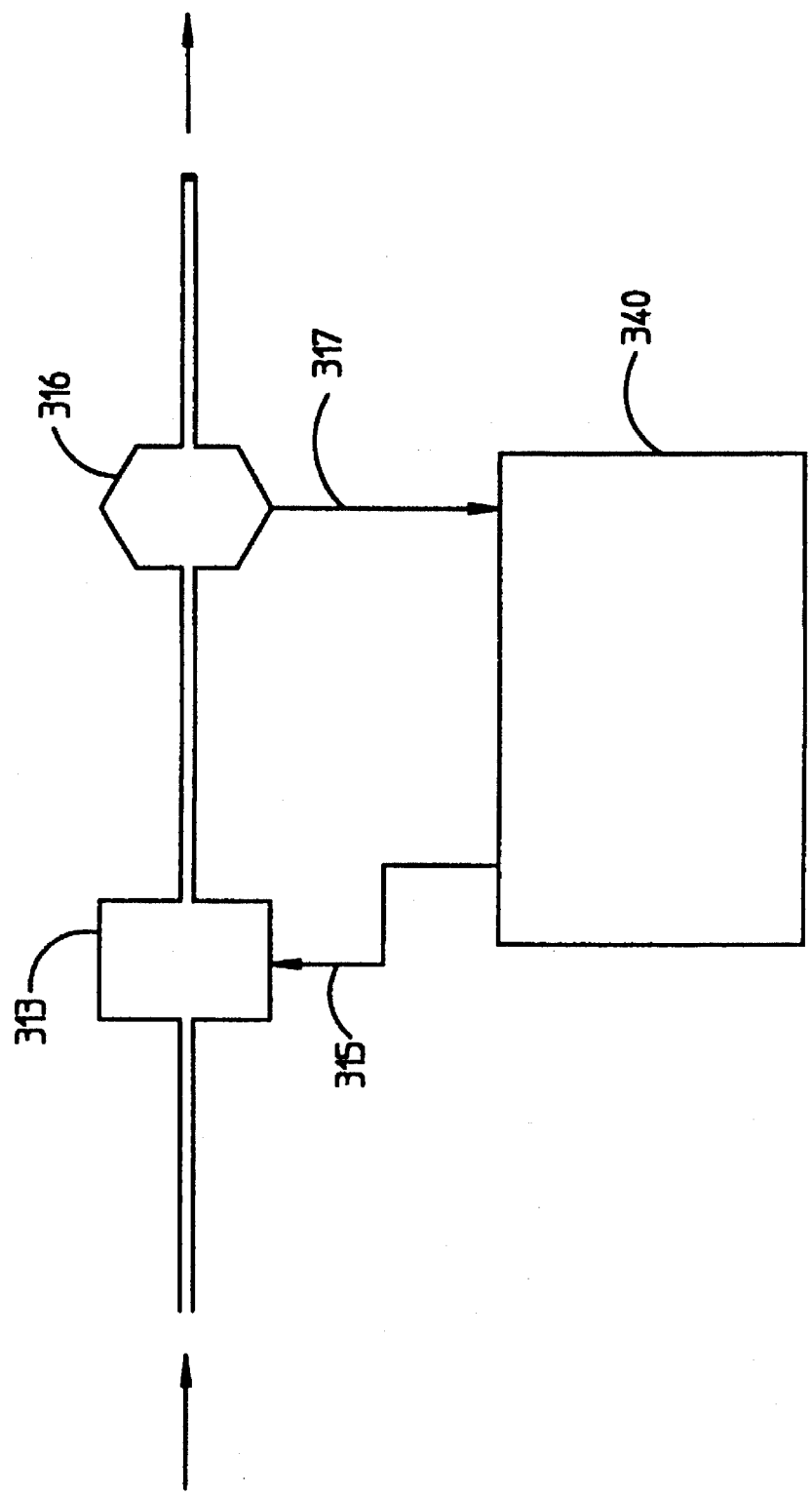
FIG. 3 depicts a temperature compensated flow regulating device as set forth in the preferred embodiment.

FIG. 3 is a block diagram of the invention illustrating proportional valve 313 which opens and closes in response to a temperature and pressure compensated control signal 315 which is generated by a processor 340 in accordance with the invention. The flow sensor 316 provides an output voltage 317 which is modified in accordance to stored characteristic equations of the flow sensor.

Figure 4:
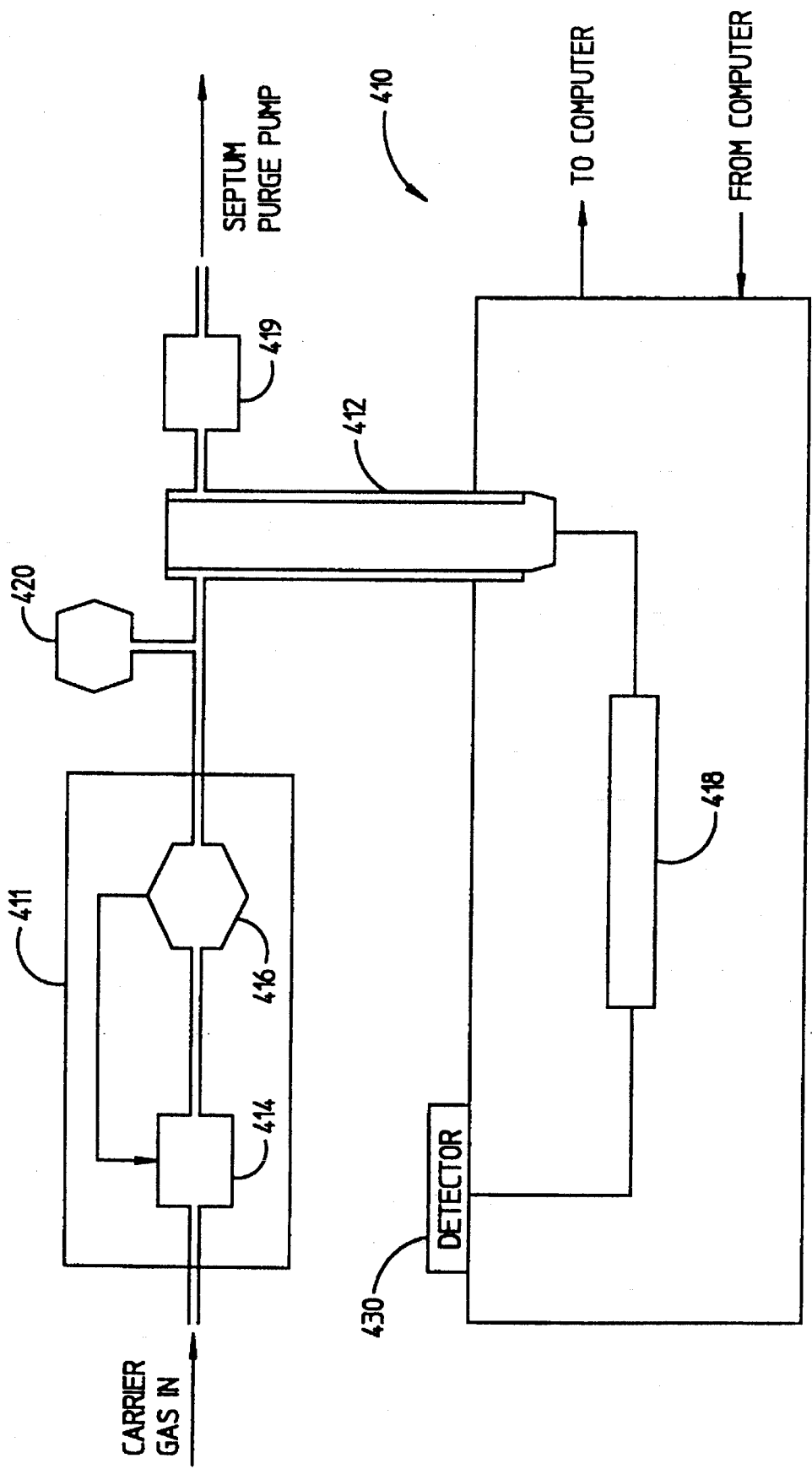
FIG. 4 depicts a gas chromatograph having a packed column inlet and a temperature compensated flow regulating device.

FIG. 4 illustrates a preferred embodiment of the invention incorporated into a gas chromatograph having an inlet for a packed column 418. To perform a chromatographic separation of a given sample compound, the sample is injected into a pressurized carrier fluid through injection port 412. The carrier fluid supplied to injection port 412 is first provided from a source (not shown) to a mass flow controller 411 comprising proportional valve 414 and temperature and pressure compensated flow sensor 416 which regulates total inlet flow. Inlet pressure of the carrier fluid is measured by the temperature and pressure compensated pressure sensor 420. The pressure of the carrier fluid is controlled by valve 414 in response to an appropriate signal from the controller described in relation to FIG. 7. Regulator 418 is employed for controlling the septum purge flow.

Figure 5:
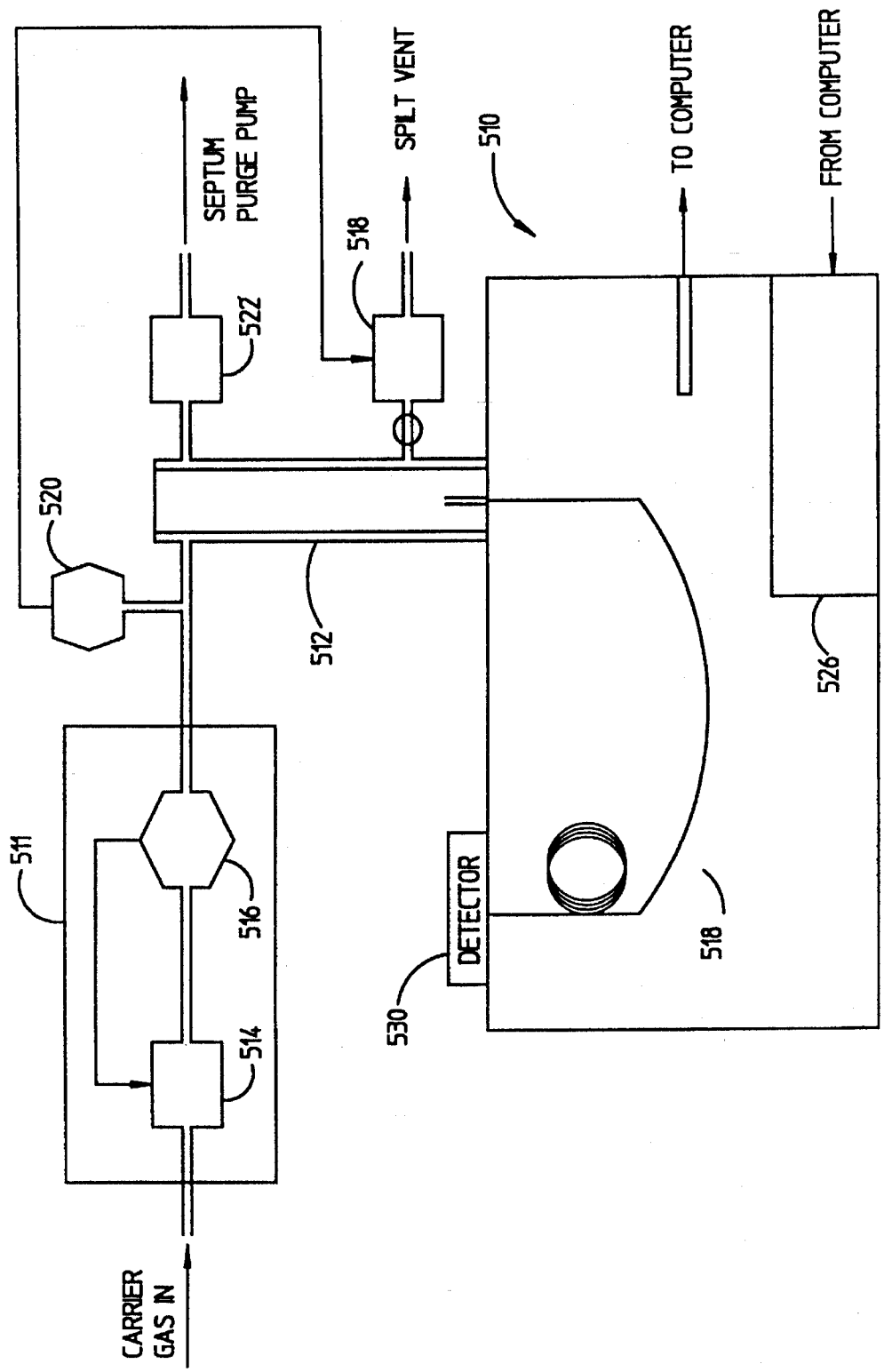
FIG. 5 depicts a back pressure regulated gas chromatograph having a temperature and pressure compensated flow regulating device.

FIG. 5 is a block diagram of the invention employed in combination with a proportional valve to control fluid flow into the inlet of a forward pressure regulated gas chromatograph 510. To perform a chromatographic separation of a given sample compound, the sample is injected into a pressurized carrier fluid through injection port 512. The carrier fluid supplied to injection port 512 is first provided from a source (not shown) to a mass flow controller 511 comprising proportional valve 514 and temperature and pressure compensated flow sensor 516 which regulate total inlet flow. Valve 518 is a back pressure regulator and serves to control the inlet pressure of the carrier fluid as measured by the temperature and pressure compensated pressure sensor 520. The total carrier fluid is provided directly to injection port 512 from mass controller 511. The pressure of the carrier fluid is controlled by valve 520 in response to an appropriate signal from the controller described in relation to FIG. 7. Regulator 522 is employed for controlling the septum purge flow. Valve 524 is an on/off valve which is opened during a split injection.

Figure 6:
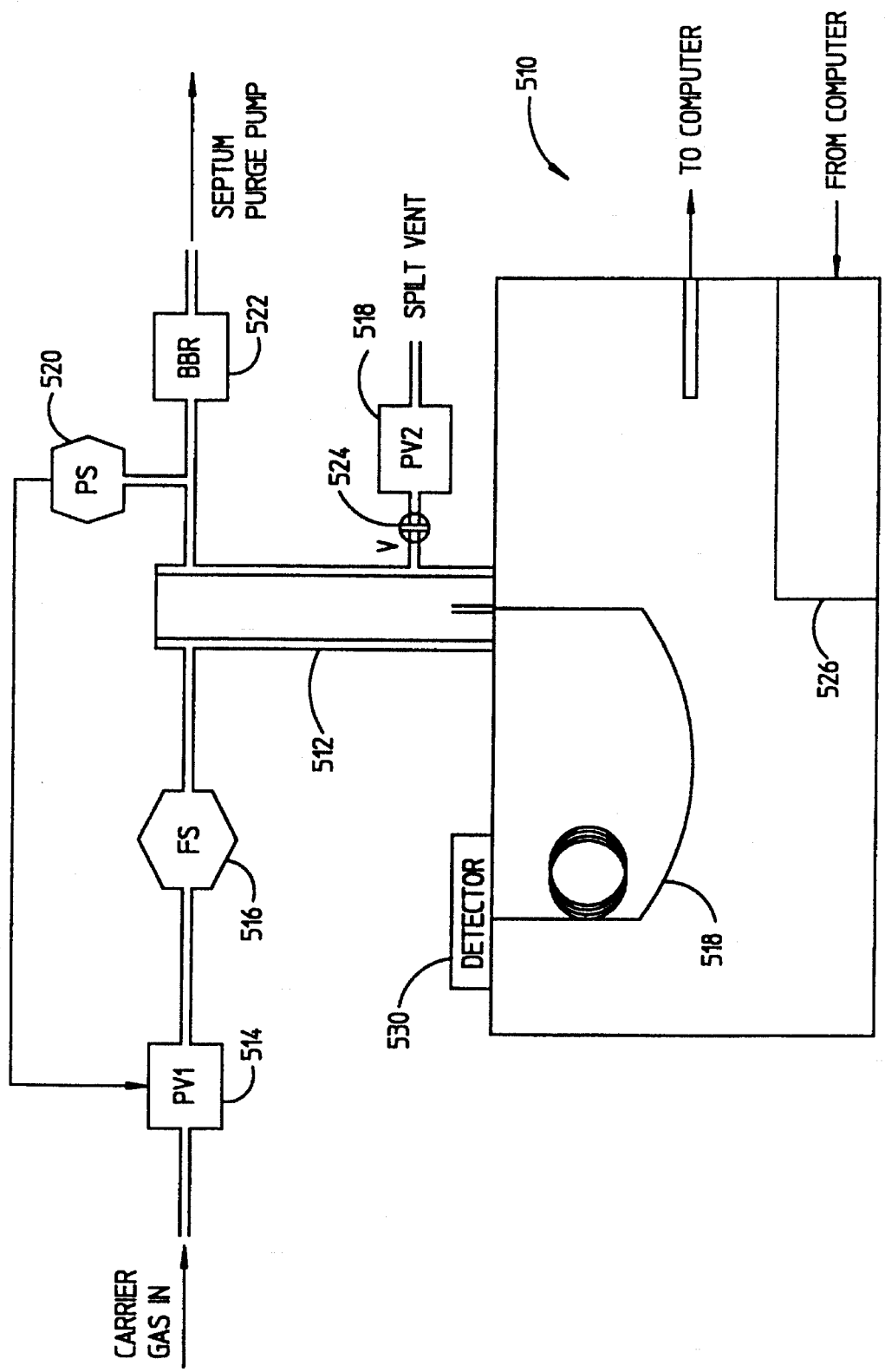
FIG. 6 depicts a forward pressure regulated gas chromatograph having a temperature and pressure compensated forward flow sensing device.

FIG. 6 illustrates an alternative arrangement in which the gas chromatograph 510 set up for a splitless injection in which valve 514 is used to control the pressure as measured by the temperature and pressure compensated pressure sensor 520. The valve 524 is turned off so that there is no flow out of the split vent. Flow sensor 516 measures total flow, but it does not control valve 514. In this configuration, the total flow into the inlet 512 is the column flow plus the septum purge flow. Injection port 512 provides a portion of the carrier fluid/sample combination to column 518 with the remainder passing through a non-analyzed output 522. The flow exiting output 22 is known as the septum purge flow. The pressure of the carrier fluid is controlled by valve 14 in response to an output from sensor 20 which is employed for generating an appropriate signal as described in relation to FIG. 7.

Figure 7:
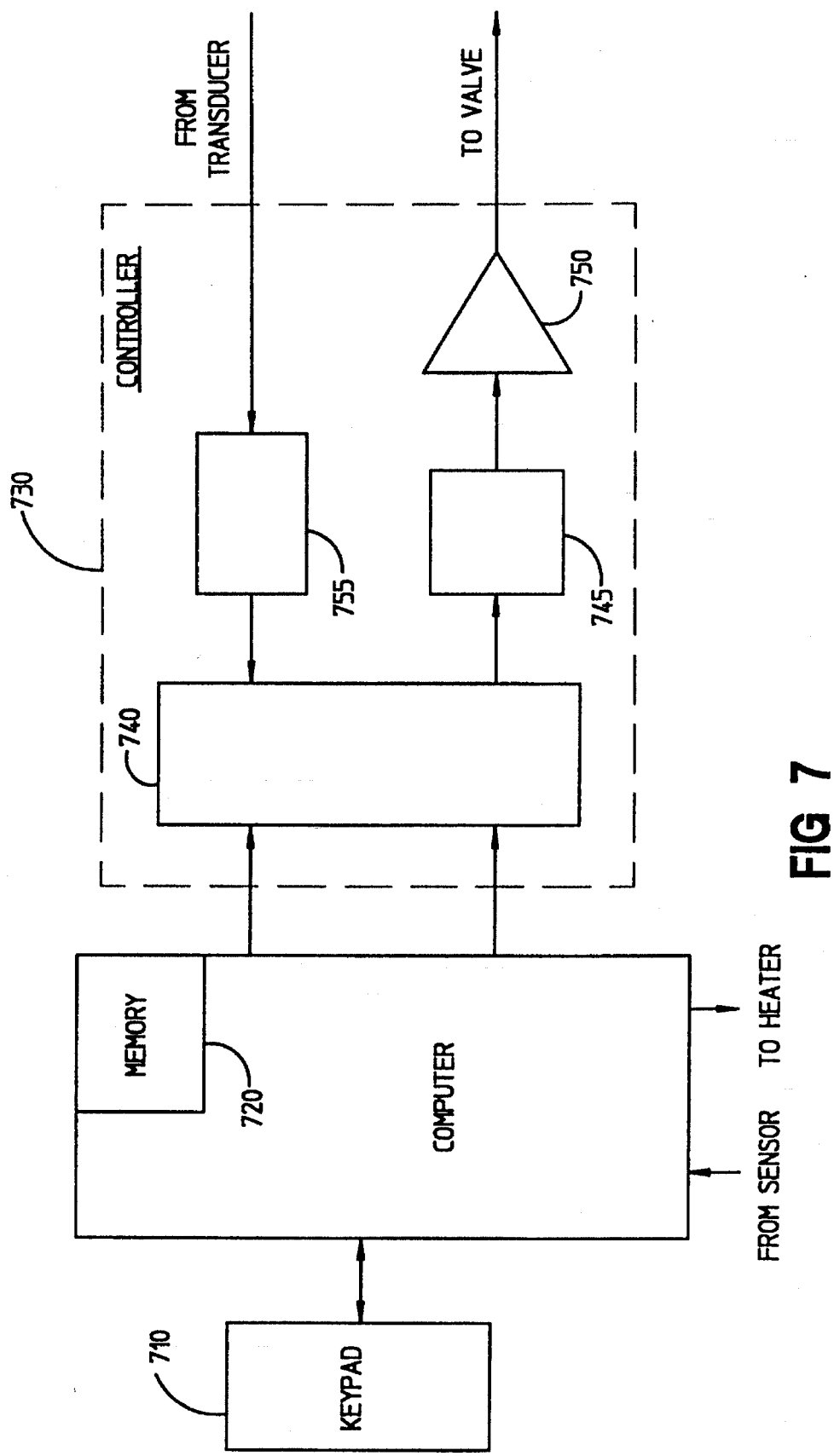
FIG. 7 depicts the control system for the gas chromatograph's illustrated in FIG. 5 and FIG. 6.
Figure 8:
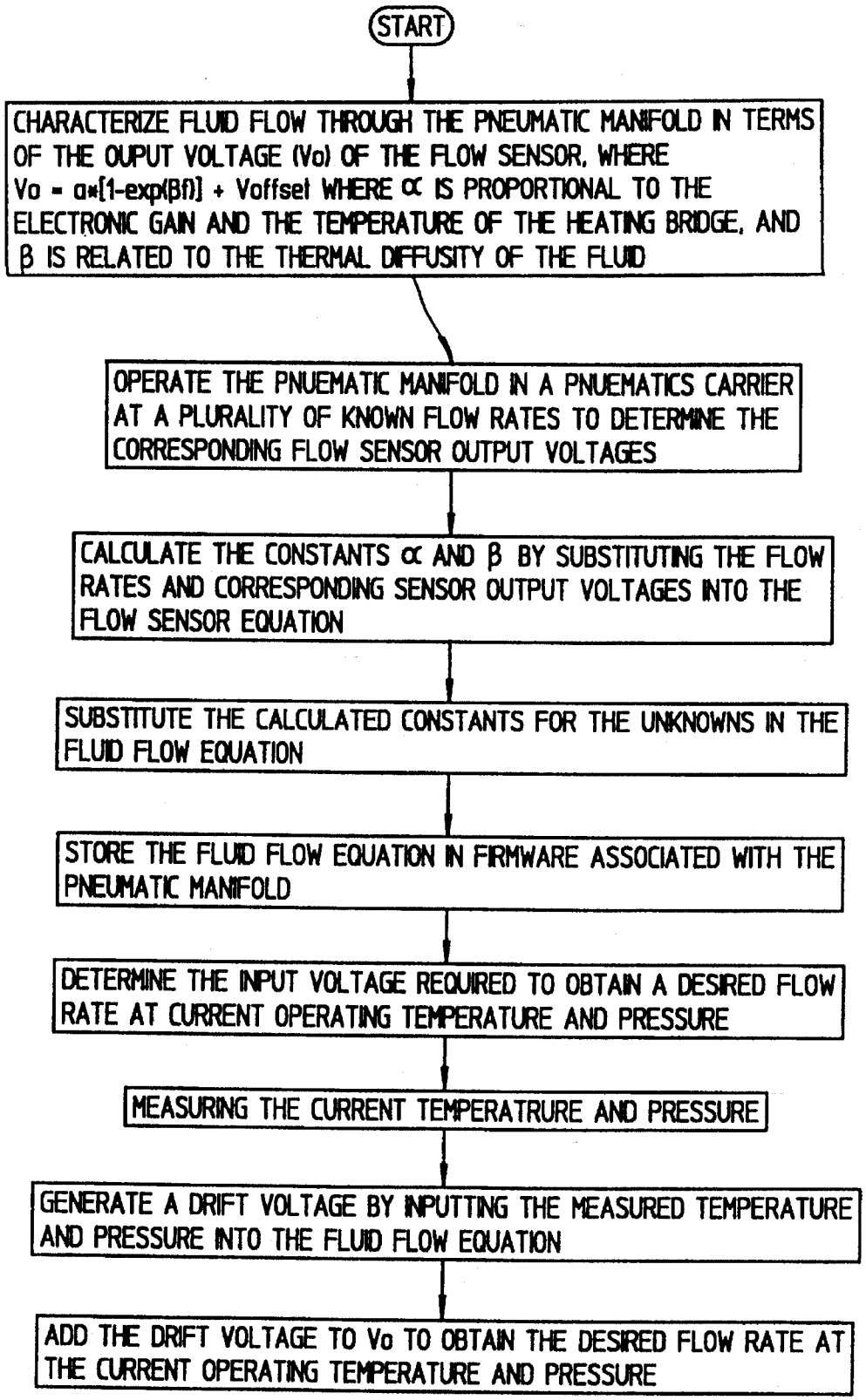
FIG. 8 is a flow chart illustrated the inventive steps employed for calibrating the flow sensor and pressure sensor illustrated in FIG. 5 and FIG. 6.

The electronic controls utilized in accordance with the principles of the present invention to operate the chromatograph's shown in FIGS. 5 and 6 will hereafter be described. Referring to FIG. 7, the electronic controls are shown to include three main components, namely keypad 710, computer 720 and controller 730. Computer 720 maintains overall control of all systems associated with gas chromatograph 510. It will be recognized that although computer 720 is shown as a single block, such computer includes a central processing unit and all assorted peripheral devices such as random access memories, read-only memories, input/output devices, and related components. Alternatively, the computer may be a processor and memory on board the instrument, which employs the instrument keypad as the user interface. Such stand alone instruments are frequently operated in combination with a PC to provide added functionality.

A controller circuit 730 is utilized to control either valve 514 or 518 illustrated in FIGS. 5 and 6. Controller 730 is shown to include a second computer 740. Computer 740 in the preferred embodiment generates a control signal which is used to control valves 514 and 518. Since the generated control signal is in a digital form it is converted to analog form by digital to analog converter 745 and appropriately amplified by amplifier 750 prior to transmission to valve 514 and/or 518. The carrier fluid flow as sensed by flow sensor 516 or pressure as sensed by pressure sensor 520 is provided to computer 740 by first converting the analog signal generated by the sensors from analog to a digital signal by converter 755. The digital signal generated by converter 755 is supplied to computer 740.

II. Generation of Mass Flow, Temperature Drift and Pressure Sensor Model Equations As previously set forth, compensation for changes in the current operating temperature and pressure may be obtained by storing equations which characterize fluid flow and accessing them during operation to provide drift voltages for modification of flow and pressure sensor output voltages.

A. Mass Flow Equation

A characteristic equation of fluid flow through the pneumatic manifold in terms of the output voltage (Vo) of the flow sensor is generated and stored in firmware. In particular, $$Vo = \alpha * [1 - exp(\beta f)] + Voffset$$

where $\alpha$ is proportional to the electronic gain and the temperature of the heating bridge, and $\beta$ is related to the thermal diffusivity of the fluid. The characteristic equation has three unknowns related to each active component in the pneumatic manifold. In order to identify these unknown voltage levels, the manifold is operated in a pneumatics test stand at a plurality of different flow rates. The sensor output voltage may be obtained in two ranges by measuring at zero flow rate to determine Vdrift, at flow rate f to determine the sensor output voltage Vo1+Vdrift, and at flow rate 3f to determine the sensor output voltage Vo3+Vdrift. The constants can be calculated by substituting the sensor output voltages into the flow sensor equation. Once these constants have been determined, they are then stored in firmware.

B. Thermal Drift Equation

The effect of thermal drift on flow sensitivity may be compensated for by characterizing thermal drift as the derivative of the flow sensor equation:

$$dVo/dT = (Von/\alpha)(d\alpha/dT) - \alpha/\beta * Ln[1-(Von/\alpha)] * [1-(Von/\alpha)] d\beta/dT + dVoffset/dT$$

where Vo is the sensor output voltage and Von is the sensor output voltage minus the zero flow sensor output voltage. Once characterized, the unknown constants $d\alpha/dt$ (proportional to the drift of the electronic gain and the temperature of the heating bridge), $d\beta/dT$ (proportional to the drift of the thermal diffusity of the gas) and DVoffset/dt (electronic drift voltage) can be calculated by measuring temperature drift at no flow, and at two other flow settings.

C. Pressure Sensor Model $$C_p = (A + B*p_1) + (dC_p/dt_c)*t_c$$

where:

$C_p$ = sensor response (A/D counts)

A = drift at 0 degC. and 0 psig (A/D counts)

B = pressure sensitivity (counts/psi)

$p_1$ = source gauge pressure (psig) = $P_s$ − [atmos pressure]

$t_c$ = thermistor temperature (deg C.)

$$dC_p/dt_c = C + D*p_1$$

where:

C = temperature sensitivity (A/D counts per degC.)

D = pressure sensitivity change with temperature (A/D counts per psi per degC.)

II. Calibration

Each component of the system (flow restrictor, pressure sensor, manifold, temperature sensor) has inherent variations such that the complete system should be calibrated. A pneumatics carrier replicating real operating conditions is employed for calibrating at several temperatures and pressures. Through calibration, the constants set forth in the models stored in firmware can be ascertained. In particular, for each pressure sensor, data must be gathered which relates pressure to A/D counts at two pressures (one can be 0 psig), each of which are conducted at two different temperatures (one temperature nominally 35 deg). For each flow restrictor, data must be gather to characterize fluid flow versus pressure at two points (each with flow) at nominal 35 deg C.; required for each fluid used in the channel. For the Thermistor Model, data must be gathered which characterizes temperatures vs A/D counts at two points.

The plurality of flow rates employed for defining the constants may include, zero flow rate to determine Vdrift, at flow rate f to determine the sensor output voltage Vo1+Vdrift, and at flow rate 3f to determine the sensor output voltage Vo3+Vdrift. To maintain accuracy over a larger non-linear range of flow rates, sensor output voltages are calculated at two separate ranges, for example, 0f and 3f, and 3f to 9f, by obtaining sensor output voltages at three flow rates 0f, 3f and 9f.

In order to determine the unknown constants of the pressure sensor, the manifold is operated in a pneumatic test stand at a plurality of known pressures such that the pressure sensor output voltages can be measured. The constants in each equation are obtained by taking the equations formed by substituting in the measured pressure sensor output voltages and the known flow rates and solving them simultaneously to obtain the unknown constants. The derivative of this equation (including the constants) characterizes the pressure sensor drift voltage ($dC_p/dt_c = C + D*p_1$). By inserting measured ambient temperature and pressure values into this equation during operation a pressure sensor drift voltage is generated. This drift voltage is combined with the pressure sensor output voltage to form a modified pressure sensor output voltage. Alternatively, a look-up table associating a range of expected fluid pressures to output voltages, as well as output voltages to pressure is created prior to operation and accessed during operation upon measurement of the current ambient temperature and pressure. These steps are repeated continuously to provide closed loop control of the desired flow rates pressure.

III. Implementation in a Gas Chromatograph

Upon initialization of a gas chromatograph, a plurality of fluid flow rates and the corresponding output voltages are input into the characterizing equations stored in firmware to generate look-up tables which relate fluid flow to output voltage Vo, and output voltage Vo to fluid flow at a plurality of ambient temperature and pressure conditions. The voltage level of a control signal required to achieve a desired flow rate at ambient temperature and pressure is first determined and stored in memory. During instrument operation, current temperature and pressure are constantly monitored such that upon a request for a desired flow rate, the look-up table can be accessed to determine the appropriate drift voltage level required for addition to the input voltage Vo to nullify the effects caused by changes in ambient conditions and provide the desired flow rate. The drift voltage is then added to Vo to obtain the desired flow rate at current operating temperature and pressure. These steps are repeated continuously to provide closed loop control of the desired detector conditions.

While the invention has been described and illustrated with reference to specific embodiments in the area of gas chromatography, those skilled in the art will recognize that modification and variations may be made such that the invention is equally applicable to the field automotive engine design, or other fields where compensation for changes in ambient temperatures and pressures is required for measurement and control of fluid supplies. For example, the fuel/air mixture of an automotive engine is typically controlled by measuring air flow through an intake manifold and then controlling the amount of fuel injected into the intake manifold. The invention is very applicable to this application an may be employed to enhance engine operating efficiency and performance.

What is claimed is:

1. An analytical instrument having an electronically controlled pneumatic manifold in which the effects of current operating temperature and pressure variations on fluid flow are compensated for to provide accurate control of inlet fluid flows, comprising:

a source of fluid, a manifold body made of heat conductive material such that the manifold remains at current operating temperature, a fluid pressure sensor, mounted in thermal contact with said manifold body, for generating a fluid pressure signal corresponding to the pressure of the fluid between the pressure regulator and the inlet, pressure sensor, mounted in thermal contact with said manifold body, for generating a current operating pressure signal corresponding to the current operating pressure, a temperature sensor, mounted in thermal contact with said manifold body, for generating a temperature signal corresponding to the temperature of the manifold, a plurality of equations stored in firmware which model fluid flow through the flow sensor, fluid pressure from the fluid source, temperature at the temperature sensor and the effect of current operating pressure on fluid flow, a computer for generating a control signal based on the temperature signal, fluid pressure signal and current operating pressure signal and the plurality of model equations stored in firmware, and an electronic control valve mounted in thermal contact with said manifold body, which adjusts the pressure of the fluid between the fluid source and the inlet in response to the control signal.

2. The electronically controlled pneumatic manifold as claimed in claim 1, said equations for modeling fluid flow through the mass flow sensor further comprise:

$$Vo = \alpha * [1 - exp(\beta f) + Voffset$$

where $\alpha$ is proportional to the electronic gain and the temperature of the heating bridge, and $\beta$ is related to the thermal diffusivity of the fluid.

3. The electronically controlled pneumatic manifold as claimed in claim 2, further comprising an equation for modeling the upstream pressure $$C_p = A + C*t_c + (B + D*t_c)*p_1$$

where:

$C_p$ = sensor response (A/D counts)

A = drift at 0 degC. and 0 psig (A/D counts)

B = pressure sensitivity (counts/psi)

$p_1$ = source gauge pressure (psig) = $P_s$ − [atmos pressure]

$t_c$ = thermistor temperature (deg C.).

4. The electronically controlled pneumatic manifold as claimed in claim 2, wherein the derivative of the fluid flow equation, $$dVo/dT = (Von/\alpha)(d\alpha/dT) - \alpha/\beta * Ln[1-(Von/\alpha)]*[1-(Von/\alpha)] \, d\beta/dT + dVoffset/dT$$

where Vo is the sensor output voltage and Von is the sensor output voltage minus the zero flow sensor output voltage, and wherein, the unknown constants da/dt (proportional to the drift of the electronic gain and the temperature of the heating bridge), dβ/dT (proportional to the drift of the thermal diffusity of the gas) and DVoffset/dt (electronic drift voltage) are calculated by measuring temperature drift at no flow, and at two other flow rates, such that the drift voltage of the flow sensor can be calculated.

5. The electronically controlled pneumatic manifold as claimed in claim 1, said $C_t$ is equal to $E+F*T_c$ for modeling the temperature of the flow sensor in which the thermistor response in A/D counts $C_t$ is equal to $E+F*T_c$, and E=drift at 0 degC. (A/D counts), F=temperature sensitivity (A/D counts per degC.) and $t_c$=calibration temperature.

6. The electronically controlled pneumatic manifold as claimed in claim 1, further comprising an current operating pressure sensor which generates an current operating pressure signal proportional to atmospheric pressure in accordance with the relationship Pa=j(Ca).

7. The electronically controlled pneumatic manifold as claimed in claim 2, where the A/D voltage to counts relationship Ca=k(Va) (A/D counts from current operating pressure sensor), Cp=m(Vp) (A/D counts from source pressure sensor), Ct=n(Vt) (A/D counts from the temperature sensor voltage, and G=fluid properties stored in ROM, Pa=current operating pressure and Ps=source pressure.

8. The electronically controlled pneumatic manifold as claimed in claim 2, wherein said thermally conductive surface is made of aluminum.

9. The electronically controlled pneumatic manifold as claimed in claim 2, wherein the derivative of the pressure equation, $$dC_p/dt_c = C + D*p_1$$

where:

C=temperature sensitivity (A/D counts per degC.)

D=pressure sensitivity change with temperature (A/D counts per psi per degC.)

is employed for obtaining a pressure drift signal.

10. The electronically controlled pneumatic manifold as claimed in claim 1, wherein the flow sensor is calibrated at a pressure of 0f, 3f and 9f.

11. A method for compensating the output of a flow sensor having a heating bridge for temperature and pressure changes, comprising the method steps of:

characterizing fluid flow through the flow sensor in terms of the flow sensor output voltage (Vo), wherein the flow sensor equation is represented as:

$$Vo = \alpha*[1 - exp(\beta f)] + Voffset$$

where $\alpha$ is proportional to the electronic gain and the temperature of the heating bridge, and $\beta$ is related to the thermal diffusity of the fluid, operating the pneumatic manifold in a pneumatics test stand at a plurality of known flow rates to determine the corresponding flow sensor output voltages, calculating the constants $\alpha$ and $\beta$ by substituting the flow rates and corresponding sensor output voltages into the flow sensor equation, substituting the calculated constants for the unknowns in the fluid flow equation, taking the derivative of the fluid flow equation and storing it in computer memory associated with the pneumatic manifold, measuring the current temperature and pressure, generating a drift voltage by inputting the measured temperature and pressure into the derivative of the fluid flow equation, adding the drift voltage to flow sensor output voltage Vo to obtain an output voltage which has been compensated for changes in the current operating temperature and pressure.

12. The method for compensating the output of a fluid flow sensor as claimed in claim 11, wherein the step of generating a drift voltage further comprises, generating a plurality of look-up tables based on the fluid flow equation which relate fluid flow to output voltage Vo, and output voltage Vo to fluid flow, inputting the measured temperature and pressure into the look-up table to determine the corresponding drift voltage.

13. The method for compensating the output of a fluid flow sensor as claimed in claim 11, wherein the step of taking the derivative of the flow sensor equations further comprises the steps of:

expressing the derivative as:

$$dVo/dT = (Von/\alpha)(d\alpha/dT) - \alpha/\beta*Ln[1-(Von/\alpha)]*[1-(Von/\alpha)]d\beta/dT + dVoffset/dT$$

where Vo is the sensor output voltage and Von is the sensor output voltage minus the zero flow sensor output voltage, measuring temperature drift at no flow, and at two other flow settings, solving for the unknown constants $d\alpha/dt, d\beta/dT$ and dVoffset/dt by substituting in the measured temperature drifts into the thermal drift equation, inputting the temperature sensor output voltage into the thermal drift equation to create a temperature drift voltage, modifying the temperature sensor output voltage by adding the thermal drift voltage to the temperature sensor output voltage.

14. The method for compensating the output of a fluid flow sensor claimed in claim 11, wherein the plurality of flow rates further comprise, at zero flow rate to determine Vdrift, at flow rate f to determine the sensor output voltage Vo1+Vdrift, and at flow rate 2f to determine the sensor output voltage Vo2+Vdrift.

15. The method as claimed in claim 11, where sensor output voltages Vo1 and Vo2, minus Vdrift, are obtained at flow rates equal to f and 3f.

16. The method as claimed in claim 14, where sensor output voltages Vo1 and Vo2, minus Vdrift, are calculated in two separate ranges 0f and 3f, and 3f to 9f, by obtaining sensor output voltages at three flow rates 0f, 3f and 9f.

17. A method for regulating fluid flow through a pneumatic manifold, comprising the method steps of:

inputting a desired fluid flow rate, calculating the control signal voltage levels required to achieve the desired flow rate at current operating temperature and pressure, measuring the current temperature and pressure, calculating the change in control signal voltage levels required to achieve the desired flow rate at the current temperature and pressure in accordance with the following equation:

$$Vo = \alpha*[1 - exp(-\beta f)] + Voffset$$

where $\alpha$ is proportional to the electronic gain and the temperature of the heating bridge, and $\beta$ is related to the thermal diffusity of the fluid, wherein the flow sensor has been calibrated in a pneumatics carrier at zero flow rate to determine Vdrift, at flow rate f to determine the sensor output voltage Vo1+Vdrift, and at flow rate 2f to determine the sensor output voltage Vo2+Vdrift, calculating the constants $\alpha$ and $\beta$ by substituting the sensor output voltages into the flow sensor equation.

18. The method for calibrating the mass flow and pressure sensors of a pneumatic manifold as claimed in claim 1, the method step of looking up an drift voltage further comprising, interpolating between look-up table entries to obtain a more accurate drift voltage.

* * * * *